United States Patent [19]
Wright

[11] 3,946,042
[45] Mar. 23, 1976

[54] 3-DIETHYLAMINO-2,2-DIMETHYLPROPYL CINNAMATES

[75] Inventor: George C. Wright, Norwich, N.Y.

[73] Assignee: Morton-Norwich Products, Inc., Norwich, N.Y.

[22] Filed: May 23, 1974

[21] Appl. No.: 472,730

[52] U.S. Cl............ 260/340.5; 260/473 R; 260/477; 424/282; 424/308
[51] Int. Cl.² ................ C07C 69/76; C07D 317/68
[58] Field of Search............. 260/340.5, 473 R, 477

[56] References Cited
UNITED STATES PATENTS

| | | | |
|---|---|---|---|
| 2,103,265 | 12/1937 | Lott | 260/477 |
| 2,251,287 | 8/1941 | Lott | 260/477 |

OTHER PUBLICATIONS

Matti et al., Bull. Soc. Chim., 2 (1935), pp. 1742–1744.

*Primary Examiner*—Richard L. Raymond
*Attorney, Agent, or Firm*—Anthony J. Franze

[57] ABSTRACT

The title compounds are useful gastrointestinal antispasmodics.

4 Claims, No Drawings

3-DIETHYLAMINO-2,2-DIMETHYLPROPYL CINNAMATES

This invention is concerned with a series of 3-diethylamino-2,2-dimethylpropyl cinnamates of the formula:

CH=CHCOOCH$_2$C(CH$_3$)$_2$CH$_2$N(C$_2$H$_5$).HCl

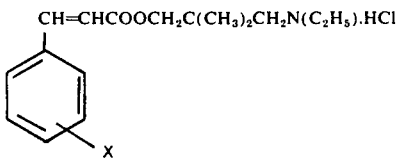

wherein X is 4-chloro, 3,4-dimethoxy or 3,4These compounds are useful pharmacologic agents. They are particularly noteworthy for their ability to produce antispasmodic effects. Thus, when administered intravenously in physiological acceptable menstrua such as isotonic saline in a dose of from 5–10 mg/kg to dogs, they abolish duodenal contractions elicited by intermittent vagus nerve stimulation. This effect is secured without prejudice to duodenal contractile response engendered by acetylcholine in contradistinction to the inhibition of such contractile response evoked by an analogous compound 3-diethylaminopropyl 3,4-dimethoxy cinnamate hydrochloride.

The compounds of this invention are readily prepared. Currently their preparation is most easily effected by reacting the appropriate cinnamic acid chloride with 3-diethylamino-2,2-dimethylpropanol. Other commonly employed methods for preparing esters would serve.

In order that this invention may be readily understood by and available to those skilled in the art, the following illustrative examples are supplied.

EXAMPLE I

3-Diethylamino-2,2-dimethylpropyl 3,4-methylenedioxycinnamate hydrochloride 3,4-methylenedioxycinnamic acid (15 g, 0.08 mole) was added to thionyl chloride (30 ml) with rapid stirring and then refluxed for 3 hours. The mixture was stripped of excess thionyl chloride, benzene (100 ml) was added, and the mixture was again stripped of solvent. The residue was treated with a solution of 3-diethylamino-2,2-dimethylpropanol (12.8 g, 0.08 mole) in benzene (400 ml), refluxed for 3 hours, cooled, diluted with petroleum ether (500 ml) and stored overnight at room temperature. The benzene-petroleum ether solution was decanted, the residue dissolved in H$_2$O (500 ml), adjusted to pH 10 with saturated aqueous K$_2$CO$_3$, and the product was extracted with CHCl$_3$ (600 ml). The CHCl$_3$ extract was dried overnight over MgSO$_4$ and Darco, filtered, and the filtrate was stripped of solvent under reduced pressure. The product was dissolved in ether (800 ml) and the solution was adjusted to pH 2 with a solution of dry HCl in ether. The product crystallized with scratching and was collected by filtration. Yield: 18 g (61%). A sample was recrystallized from ethyl acetate, m.p. 152°–154°.

Anal. Calcd. for C$_{19}$H$_{27}$NO$_4$.HCl: C, 61.69; H, 7.63; N, 3.79. Found: C, 61.48; H, 7.71; N, 3.75.

EXAMPLE II

3-Diethylamino-2,2-dimethylpropyl-p-chlorophenylcinnamate hydrochloride p-Chlorocinnamic acid (27.5 g, 0.15 mole) was added with rapid stirring to thionyl chloride (52.5 ml) and refluxed for 3½ hours. The mixture was stripped of excess thionyl chloride under reduced pressure, benzene (100 ml) was added and the mixture was again stripped of solvent. The residue was treated with a solution of 3-diethylamino-2,2-dimethylpropanol (24.2 g, 0.15 mole) in benzene (500 ml), refluxed for 3 hours, cooled, diluted with petroleum ether (500 ml), and stored overnight at room temperature. The benzene-petroleum ether solution was decanted, the residue dissolved in H$_2$O (700 ml) and the solution adjusted to pH 10 with saturated aqueous K$_2$CO$_3$ (60 ml). The product was extracted from the aqueous phase with benzene (800 ml) in portions and the extract dried overnight over MgSO$_4$ and Darco. The solution was filtered and the filtrate adjusted to pH 2 with a solution of dry HCl in ether (cooled in an ice bath). Petroleum ether (500 ml) was added and the product oiled out of solution. The benzene-petroleum ether solution was decanted and the product was recrystallized from ethyl acetate (600 ml), yield: 33 g (61%). A sample was recrystallized from ethyl acetate, m.p. 132°–134°.

Anal. Calc'd for C$_{18}$H$_{26}$ClNO$_2$.HCl: C, 60.00; H, 7.55; N, 3.89. Found: C, 59.75; H, 7.76; N, 3.91.

EXAMPLE III

3-Diethylamino-2,2-dimethylpropyl 3,4-dimethoxyphenylcinnamate hydrochloride 3,4-Dimethoxycinnamic acid (31.4 g, 0.15 mole) was added with rapid stirring to thionyl chloride (52.5 ml) and refluxed for 4 hours. The mixture was stripped of excess thionyl chloride under reduced pressure, benzene (100 ml) was added, and the mixture was again stripped of solvent. The residue was treated with a solution of 3-diethylamino-2,2-dimethylpropanol (24.2 g, 0.15 mole) in benzene (500 ml), refluxed for 3 hours, cooled, diluted with petroleum ether (500 ml), and stored overnight at room temperature. The benzene-petroleum ether solution was decanted, the residue dissolved in H$_2$O (800 ml), and the solution adjusted to pH 8 with saturated aqueous K$_2$CO$_3$ (60 ml). The product was extracted from the aqueous phase with benzene (800 ml) in portions and the extract dried overnight over MgSO$_4$ and Darco. The solution was filtered and the filtrate adjusted to pH 3 with a solution of dry HCl in ether (cooled in ice bath). Petroleum ether (500 ml) was added and the product oiled out of solution. The benzene-petroleum ether solution was decanted, chloroform (5–0 ml) was added and the mixture was stripped to dryness under reduced pressure. This procedure was repeated three times and then the residue was washed with anhydrous ether (scratching induced crystallization). The product was collected by filtration, yield: 34 g (59%). A sample was recrystallized from ethyl acetate, m.p. 135°–138°.

Anal. Calc'd for C$_{20}$H$_{31}$NO$_4$.HCl: C, 62.24; H, 8.36; N, 3.63. Found: C, 62.43; H, 8.37; N, 3.62.

What is claimed is:

1. A compound of the formula:

CH=CHCOOCH$_2$C(CH$_3$)$_2$CH$_2$N(C$_2$H$_5$)$_2$.HCl

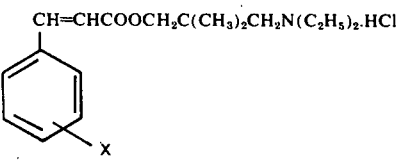

wherein X is 4-chloro, 3,4-dimethoxy or 3,4-methylenedioxy.

2. The compound of claim 1 wherein X is 4-chloro.

3. The compound of claim 1 wherein X is 3,4-dimethoxy.

4. The compound of claim 1 wherein X is 3,4-methylenedioxy.

* * * * *